US010303848B2

United States Patent
Ochi et al.

(10) Patent No.: US 10,303,848 B2
(45) Date of Patent: May 28, 2019

(54) MEDICAL READING REPORT PREPARING APPARATUS AND MEDICAL IMAGE DIAGNOSTIC APPARATUS

(71) Applicant: Toshiba Medical Systems Corporation, Otawara-shi (JP)

(72) Inventors: Masumi Ochi, Sakura (JP); Yasuyuki Miyoshi, Nasushiobara (JP); Hiroshizu Morishima, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 975 days.

(21) Appl. No.: 14/327,657

(22) Filed: Jul. 10, 2014

(65) Prior Publication Data

US 2014/0324475 A1   Oct. 30, 2014

Related U.S. Application Data

(63) Continuation of application No. PCT/JP2013/073451, filed on Aug. 30, 2013.

(30) Foreign Application Priority Data

Aug. 31, 2012   (JP) ................................. 2012-191622

(51) Int. Cl.
G06F 17/30   (2006.01)
G06F 19/00   (2018.01)
(Continued)

(52) U.S. Cl.
CPC .......... *G06F 19/321* (2013.01); *A61B 8/0891* (2013.01); *A61B 8/488* (2013.01);
(Continued)

(58) Field of Classification Search
None
See application file for complete search history.

(56) References Cited

U.S. PATENT DOCUMENTS

2002/0111932 A1*   8/2002   Roberge ................ G06F 3/0482
2002/0190980 A1*  12/2002   Gerritsen ............... G06T 19/00
                                                                    345/419

(Continued)

FOREIGN PATENT DOCUMENTS

CN   1551033 A   12/2004
CN   1873651 A   12/2006
(Continued)

OTHER PUBLICATIONS

International Search Report dated Nov. 26, 2013 for PCT/JP2013/073451 filed on Aug. 30, 2013 with English Translation.

(Continued)

*Primary Examiner* — Anhtai V Tran
(74) *Attorney, Agent, or Firm* — Oblon, McClelland, Maier & Neustadt, L.L.P.

(57) ABSTRACT

According to one embodiment, a schema storage unit stores a reference schema that schematically expresses the internal structure of a diagnosis target blood vessel concerning the reference section of the diagnosis target blood vessel. A schema processing unit automatically generates a schema concerning a section crossing the reference section of the diagnosis target blood vessel by image processing based on the reference schema.

17 Claims, 13 Drawing Sheets

(51) Int. Cl.
*A61B 8/08* (2006.01)
*G16H 15/00* (2018.01)
*A61B 5/00* (2006.01)
*A61B 5/055* (2006.01)

(52) U.S. Cl.
CPC .............. *G16H 15/00* (2018.01); *A61B 5/055* (2013.01); *A61B 5/7425* (2013.01)

(56) References Cited

U.S. PATENT DOCUMENTS

| | | | |
|---|---|---|---|
| 2004/0015778 A1* | 1/2004 | Britton | G06F 17/211 |
| | | | 715/205 |
| 2004/0116808 A1* | 6/2004 | Fritz | A61B 5/02007 |
| | | | 600/437 |
| 2004/0249270 A1* | 12/2004 | Kondo | G06T 15/08 |
| | | | 600/425 |
| 2005/0090742 A1* | 4/2005 | Mine | A61B 8/0833 |
| | | | 600/443 |
| 2005/0203417 A1* | 9/2005 | Okuno | A61B 8/0841 |
| | | | 600/463 |
| 2006/0262134 A1* | 11/2006 | Hamiter | G06F 19/321 |
| | | | 345/619 |
| 2006/0269112 A1 | 11/2006 | Ochi | |

FOREIGN PATENT DOCUMENTS

| | | |
|---|---|---|
| JP | 2004-283373 A | 10/2004 |
| JP | 2007-007387 A | 1/2007 |
| JP | 2010-240096 A | 10/2010 |
| JP | 2012-100815 A | 5/2012 |

OTHER PUBLICATIONS

International Written Opinion dated Nov. 26, 2013 for PCT/JP2013/073451 filed on Aug. 30, 2013.
Combined Chinese Office Action and Search Report dated Feb. 10, 2015 in Patent Application No. 201380001481.1 (with English translation of categories of cited documents).

\* cited by examiner

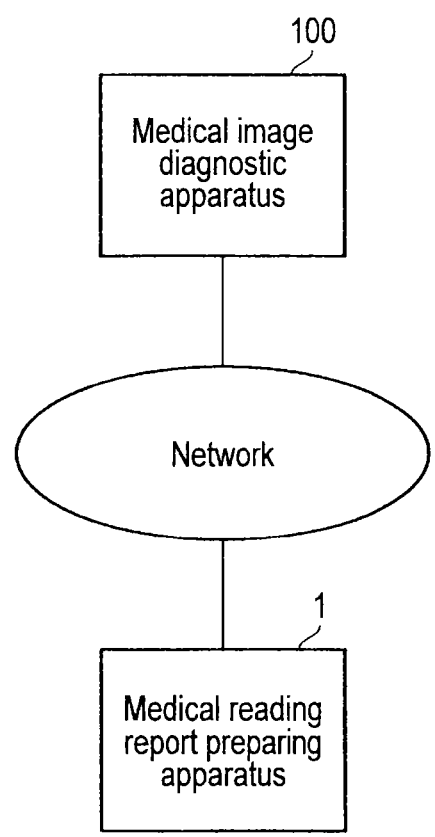
F I G. 1

Three-dimensional structure

Long-axis schema

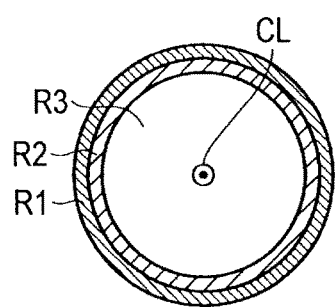
F I G. 3C

MEDICAL READING REPORT PREPARING APPARATUS AND MEDICAL IMAGE DIAGNOSTIC APPARATUS

CROSS-REFERENCE TO RELATED APPLICATIONS

This application is a Continuation application of PCT Application No. PCT/JP2013/073451, filed Aug. 30, 2013 and based upon and claims the benefit of priority from the Japanese Patent Application No. 2012-191622, filed Aug. 31, 2012 the entire contents of all of which are incorporated herein by reference.

FIELD

Embodiments described herein relate generally to a medical reading report preparing apparatus and a medical image diagnostic apparatus.

BACKGROUND

Medical reading report preparing apparatuses have become popular. Diagnostician's or technician's findings about medical images are described in a medical reading report. Schemata of a diagnosis target part are attached to the medical reading report. A schema is a diagram that schematically expresses the structure of the diagnosis target part. For example, in ultrasonic inspection of a carotid artery, schemata of long-axis sections of the carotid artery and schemata of short-axis sections are generated. The diagnostician or technician individually manually generates schemata concerning long-axis sections and schemata concerning short-axis sections via an input device such as a mouse for the shape of an intimal region or the like. Such manual schema creation places heavy load on the diagnostician or technician.

It is an object of the embodiment to provide a medical reading report preparing apparatus and a medical image diagnostic apparatus which implement reduction of working load of a user in schema generation.

BRIEF DESCRIPTION OF THE DRAWINGS

FIG. 1 is a block diagram showing the network environment of a medical reading report preparing apparatus according to an embodiment.

FIG. 3C is a view showing the typical short-axis schema of the carotid artery.

DETAILED DESCRIPTION

Figure 2:
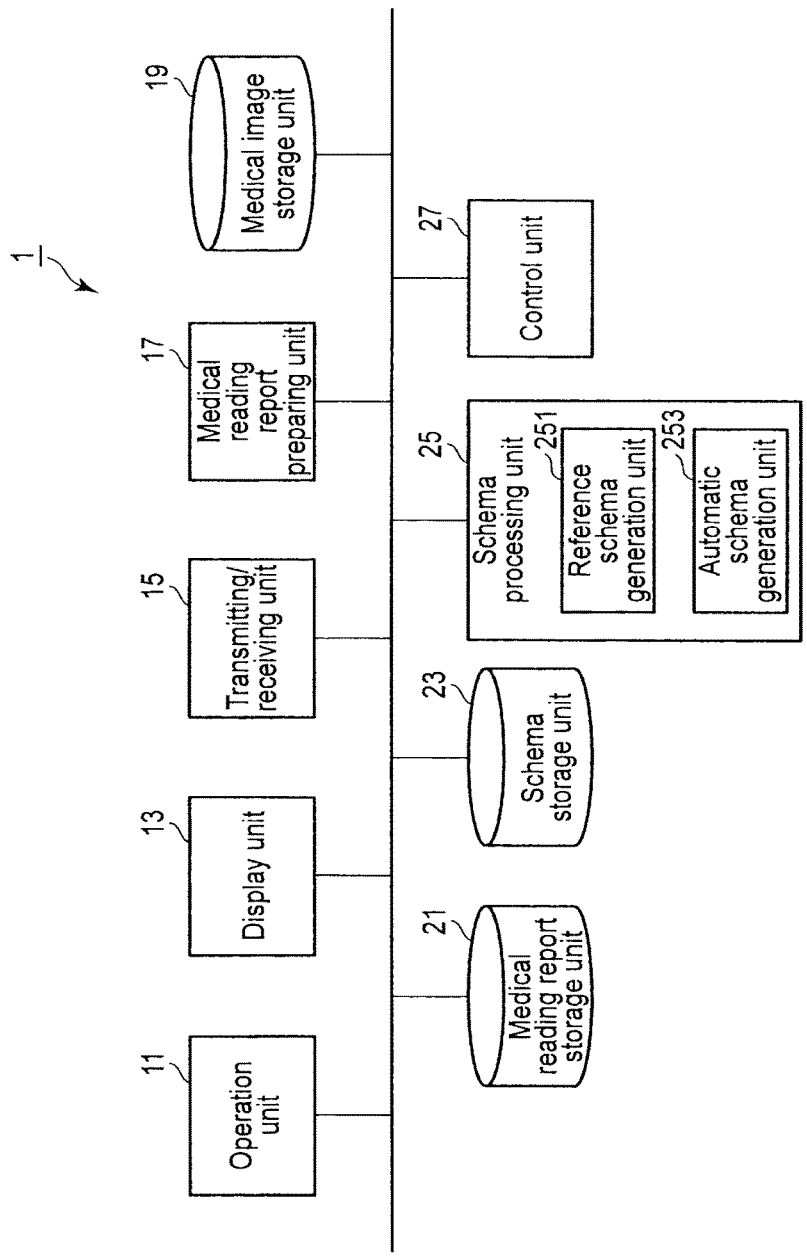
FIG. 2 is a block diagram showing the arrangement of the medical reading report preparing apparatus shown in FIG. 1.

In general, according to one embodiment, a medical reading report preparing apparatus includes a first storage unit and a generation unit. The first storage unit is configured to store a first schema that schematically expresses an internal structure of a diagnosis target blood vessel concerning a first section of the diagnosis target blood vessel. The generation unit is configured to automatically generate a second schema concerning a second section crossing the first section of the diagnosis target blood vessel by image processing based on the first schema.

A medical reading report preparing apparatus and a medical image diagnostic apparatus according to an embodiment will now be described with reference to the accompanying drawings.

FIG. 1 is a block diagram showing the network environment of a medical reading report preparing apparatus 1 according to the embodiment. As shown in FIG. 1, the medical reading report preparing apparatus 1 according to this embodiment is connected to a medical image diagnostic apparatus 100 via a network.

The medical image diagnostic apparatus 100 is a medical device that generates medical images of an object. The medical image diagnostic apparatus 100 can be an image diagnostic apparatus of any type such as an ultrasonic diagnostic apparatus, an X-ray diagnostic apparatus, an X-ray computed tomography apparatus, a magnetic resonance diagnostic apparatus, or a nuclear medicine diagnostic apparatus. A medical image generated by the medical image diagnostic apparatus 100 is transmitted to the medical reading report preparing apparatus 1. Note that the medical image need not always directly be transmitted from the medical image diagnostic apparatus 100 to the medical reading report preparing apparatus 1 but may indirectly be transmitted from the medical image diagnostic apparatus 100 to the medical reading report preparing apparatus 1. For example, the medical image is transmitted from the medical image diagnostic apparatus 100 to a PACS (Picture Archiving and Communication System) and archived. In response to a request from the medical reading report preparing apparatus 1, the medical image may be transmitted from the PACS to the medical reading report preparing apparatus 1.

The medical reading report preparing apparatus 1 is a computer apparatus used to create a medical reading report about a diagnosis target part. The medical reading report preparing apparatus 1 can be of any type such as a desktop type, a laptop type, or a tablet type. The medical reading report preparing apparatus 1 will be described below. Note that the diagnosis target part according to this embodiment is a blood vessel. The blood vessel can be a blood vessel of any part of a human body such as the head, chest, neck, heart, leg, or arm.

Note that the medical reading report preparing apparatus 1 need not always be connected to the medical image diagnostic apparatus 100 via a network as long as a medical image from the medical image diagnostic apparatus 100 can be archived. For example, the medical reading report preparing apparatus 1 may acquire a medical image stored in a recording medium such as a CD (Compact Disk), a DVD, or a portable semiconductor memory, in which medical images generated by the medical image diagnostic apparatus 100 are stored, and archive the image. In this case, the medical reading report preparing apparatus 1 need not be connected to the medical image diagnostic apparatus 100 via a network.

FIG. 2 is a block diagram showing the arrangement of the medical reading report preparing apparatus 1 according to this embodiment. As shown in FIG. 2, the medical reading report preparing apparatus 1 includes an operation unit 11, a display unit 13, a transmitting/receiving unit 15, a medical reading report preparing unit 17, a medical image storage unit 19, a medical reading report storage unit 21, a schema storage unit 23, a schema processing unit 25, and a control unit 27.

The operation unit 11 accepts various kinds of instructions from a user such as a diagnostic interpreter via an input device. As the input device, a keyboard, a mouse, various kinds of switches, and the like are usable. The input device may be a touch panel that is provided to cover the display device of the display unit 13.

The display unit 13 displays various kinds of information such as a medical image, a medical reading report preparing screen, a schema generation screen, and a schema on the display device. For example, a CRT display, a liquid crystal display, an organic EL display, a plasma display, or the like can appropriately be used as the display device.

The transmitting/receiving unit 15 transmits/receives various kinds of information to/from the medical image diagnostic apparatus 100 or another apparatus via a network. For example, the transmitting/receiving unit 15 directly or indirectly receives a medical image from the medical image diagnostic apparatus 100 via the network.

The medical reading report preparing unit 17 prepares a medical reading report that describe findings of a medical image in accordance with a user instruction input via the operation unit 11. The medical reading report is created on a medical reading report preparing screen. The medical reading report preparing unit 17 electronically attaches a schema generated by the schema processing unit 25 to be described later to the medical reading report.

The medical image storage unit 19 stores a medical image received from the medical image diagnostic apparatus 100 or PACS via the transmitting/receiving unit 15. Various kinds of additional information generated by the medical image diagnostic apparatus 100 are associated with the medical image.

The medical reading report storage unit 21 stores the medical reading report prepared by the medical reading report preparing unit 17. The medical reading report storage unit 21 may store a medical reading report supplied from another apparatus via the transmitting/receiving unit 15.

The schema storage unit 23 stores schemata of the diagnosis target blood vessel of an object, which are generated by the schema processing unit 25. The schema is a diagram that schematically expresses the internal structure of the diagnosis target blood vessel. The schema is generated to notify, for example, the structure of a diagnosis target part by an image, which is difficult to notify by a text. Schemata according to this embodiment are classified into, for example, schemata concerning short-axis sections (to be referred to as short-axis schemata hereinafter) and schemata concerning long-axis sections (to be referred to as long-axis schemata hereinafter).

Figure 3A:
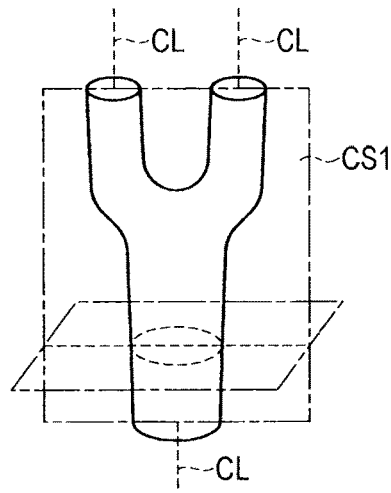
FIG. 3A is a view schematically showing the three-dimensional structure of a carotid artery.
Figure 3B:
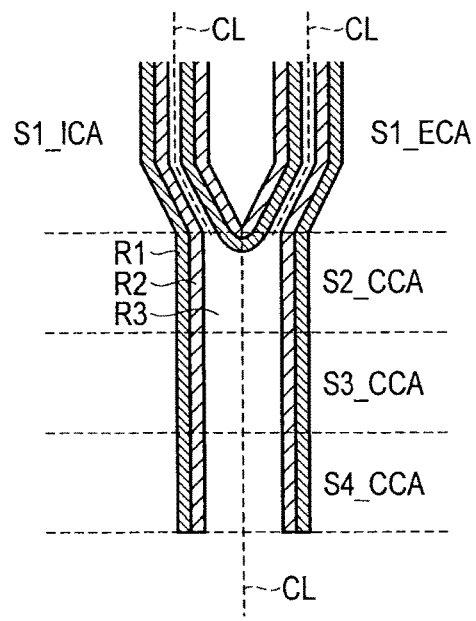
FIG. 3B is a view showing the typical long-axis schema of the carotid artery.

FIGS. 3A, 3B, and 3C are views for explaining long-axis schemata and short-axis schemata of a carotid artery. FIG. 3A is a view schematically showing the three-dimensional structure of the carotid artery. FIG. 3B is a view showing the long-axis schema of a typical carotid artery. FIG. 3C is a view showing the short-axis schema of the typical carotid artery. As shown in FIG. 3A, the carotid artery is a tubular structure having a central axis CL. The long-axis schema is defined by a schema concerning a section CS1 along the central axis CL. The short-axis schema is defined by a schema concerning a section CS2 perpendicular to the central axis CL. The section along the central axis CL will be referred to as the long-axis section CS1, and the section perpendicular to the central axis CL as the short-axis section CS2 hereinafter. The long-axis section CS1 and the short-axis section CS2 are perpendicular to each other. Each schema expresses the internal structure of the blood vessel as a stacked structure formed from a plurality of layers. For example, each schema includes three anatomical regions: a pixel region (to be referred to as an adventitial region hereinafter) R1 corresponding to the adventitia, a pixel region (to be referred to as an intimal region hereinafter) R2 corresponding to the intima, and a pixel region (to be referred to as a lumen region hereinafter) R3 corresponding to the lumen. Different pixel values are assigned to the adventitial region R1, the intimal region R2, and the lumen region R3 to visually discriminate them. The pixel values can be defined by either a gray value or a color value. The carotid artery is divided into a plurality of segments based on anatomical parts. For example, the carotid artery is divided into an ICA (Internal Carotid Artery), an ECA (External Carotid Artery), and a CCA (Common Carotid Artery), as shown in FIG. 3B or 3C. The CCA is further divided into three segments based on positions. In accordance with this classification, the carotid artery according to this embodiment is divided into five segments S1_ICA, S1_ECA, S2_CCA, S3_CCA, and S4_CCA.

Based on a schema generated in advance, the schema processing unit 25 automatically generates a schema concerning the section perpendicular to the section of the schema by image processing. The schema generated in advance can be either a short-axis schema or a long-axis schema. When the schema generated in advance is a short-axis schema, the schema automatically generated is a long-axis schema. Conversely, when the schema generated in advance is a long-axis schema, the schema automatically generated is a short-axis schema. More specifically, the schema processing unit 25 includes a reference schema generation unit 251 and an automatic schema generation unit 253. The reference schema generation unit 251 generates a schema in accordance with a user instruction input via the operation unit 11. The schema generated by the reference schema generation unit 251 will be referred to as a reference schema. The automatic schema generation unit 253 automatically generates a schema concerning the section perpendicular to the section of the reference schema by image processing. The schema generated by the automatic schema generation unit 253 will be referred to as a comparative schema hereinafter.

The section of the reference schema and that of the comparative schema are perpendicular to each other in the above explanation. However, the embodiment is not limited to this. The section of the reference schema and that of the comparative schema need only cross each other but not always perpendicularly. For example, the section of the reference schema and that of the comparative schema can make any angle such as 30°, 45°, or 60°. However, the angle made by the section of the reference schema and that of the comparative schema is assumed to be 90° for a specific description.

The control unit 27 functions as the main unit of the medical reading report preparing apparatus 1. More specifically, the control unit 27 loads a program for schema generation processing to be described later and controls the units in the medical reading report preparing apparatus 1 in accordance with the loaded program. Schema generation processing unique to this embodiment is thus executed.

Details of the medical reading report preparing apparatus 1 according to this embodiment will be described divisionally in Example 1, Example 2, and Example 3. Note that the diagnosis target blood vessel is assumed to be a carotid artery for a specific description. The medical image diagnostic apparatus 100 is assumed to be an ultrasonic diagnostic apparatus.

Example 1

A medical reading report preparing apparatus according to Example 1 automatically generates a long-axis schema based on a short-axis schema. That is, in Example 1, the short-axis schema is used as the reference schema. The medical reading report preparing apparatus according to Example 1 generates the reference schema, that is, the short-axis schema having an arbitrary internal structure in accordance with a user instruction input via an operation unit 11. A medical reading report preparing apparatus 1 according to Example 1 will be described below.

The schema is generated at the time of medical reading report creation by the user. When preparing a medical reading report, a display unit 13 displays an ultrasonic image generated by the ultrasonic diagnostic apparatus 100 and a medical reading report preparing screen. The user inputs necessary items such as findings via the operation unit 11 while observing the ultrasonic image. A medical reading report preparing unit 17 enters the necessary items such as findings input via the operation unit 11 in the format of a medical reading report.

When preparing a medical reading report, a schema processing unit 25 generates a schema. First, the user inputs a schema generation instruction via the operation unit 11. Triggered by the input of the schema generation instruction by the user via the operation unit 11, the display unit 13 displays an initial schema generation screen.

Figure 4:
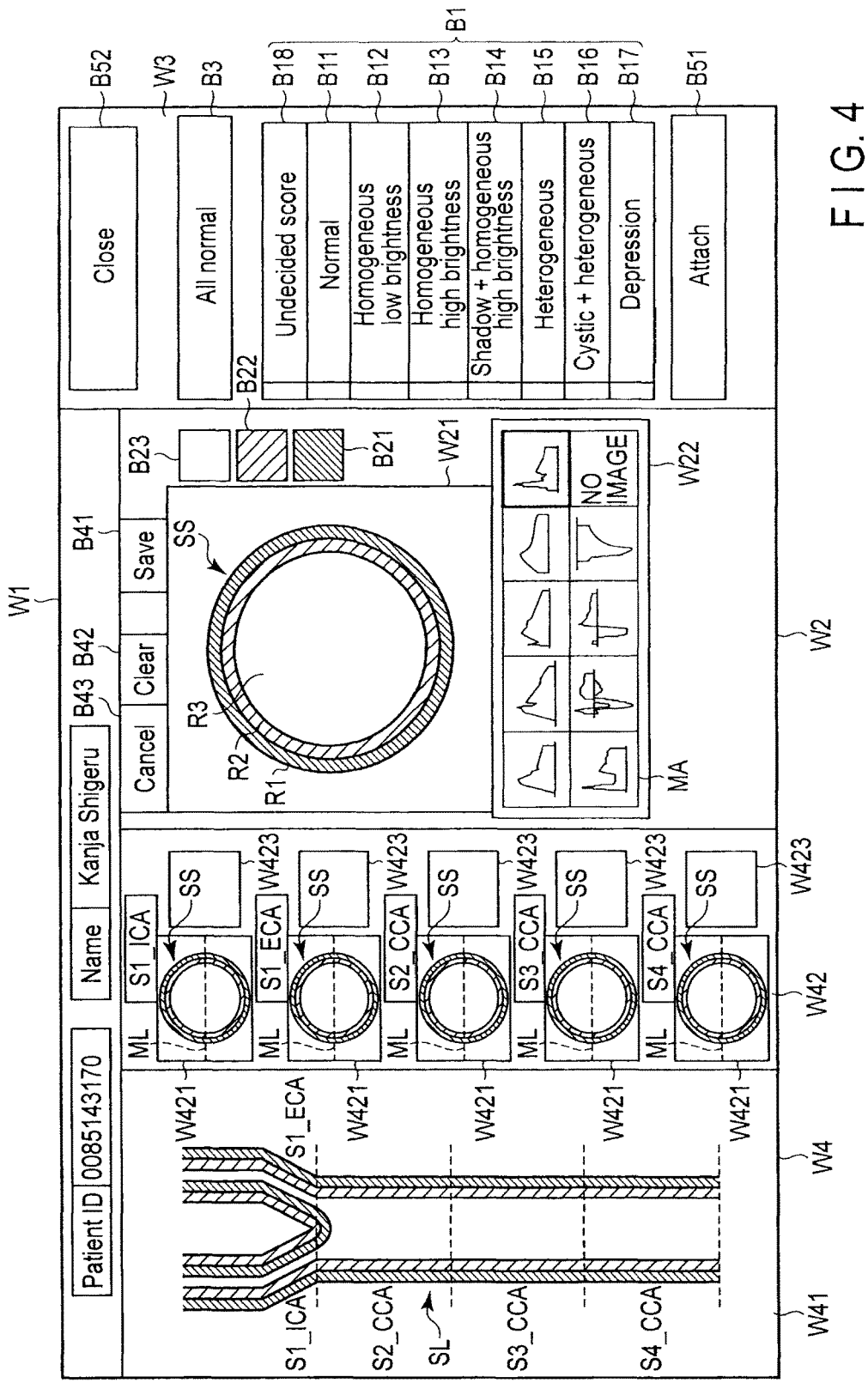
FIG. 4 is a view showing an initial schema generation screen displayed by a display unit according to Example 1.
Figure 5:
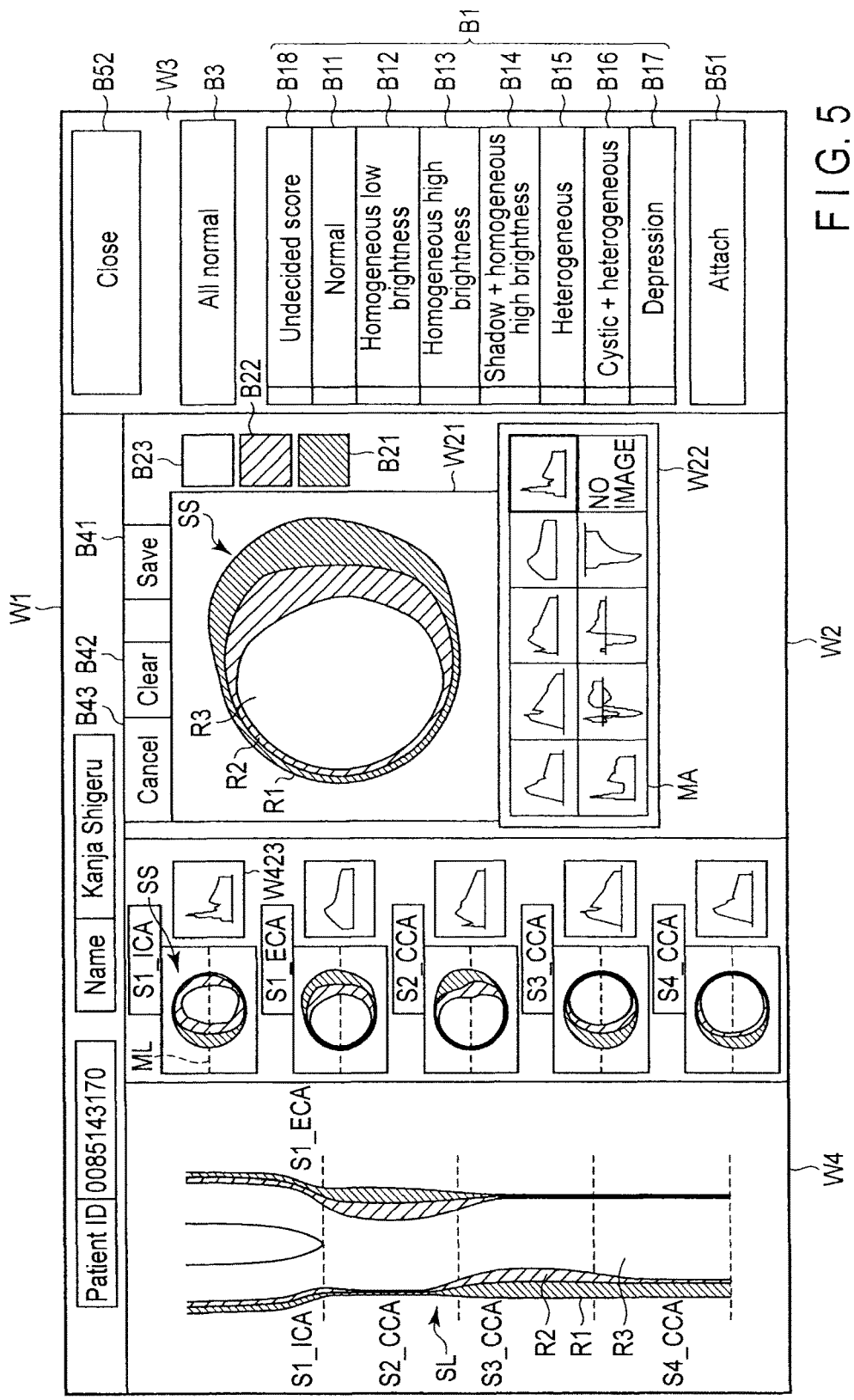
FIG. 5 is a view showing the schema generation screen after schema generation, which is displayed by the display unit according to Example 1.

FIG. 4 is a view showing the initial schema generation screen. FIG. 5 is a view showing the schema generation screen after schema generation. As shown in FIGS. 4 and 5, the schema generation screen is formed from a plurality of GUI (Graphical User Interface) parts. More specifically, the schema generation screen includes a patient information area W1, a manual generation area W2, a score area W3, and a schema area W4. The patient information area W1 is the display area of the patient information of a diagnosis target patient. An example of the patient information is a patient ID.

The manual generation area W2 is a display area used to assist manual generation of the reference schema. In Example 1, the manual generation area W2 includes a drawing area W21 and an additional diagnostic information mark area W22. The drawing area W21 is a display area used to generate a short-axis schema by a manual drawing operation via the operation unit 11. In the initial screen, the drawing area W21 displays, for example, the template of a short-axis schema SS (to be referred to as a short-axis schema template hereinafter). The short-axis schema template is a diagram that schematically expresses the typical internal structure of the short-axis section of a carotid artery blood vessel. The additional diagnostic information mark area W22 is a display area used to display a plurality of marks (to e referred to as additional diagnostic information marks hereinafter) MA expressing the contents of additional diagnostic information. The additional diagnostic information is additional information used for image diagnosis of the carotid artery. An example of the additional diagnostic information is a typical Doppler waveform pattern according to an anatomical part or diagnostic score. In this case, the mark (to be referred to as a Doppler waveform mark hereinafter) MA that schematically expresses the Doppler waveform pattern is used as the additional diagnostic information mark. Note that the additional diagnostic information is not limited to the Doppler waveform pattern. For example, the additional information may be the hemadostenosis ratio. In this case, the additional diagnostic information mark is a mark expressing the stenosis ratio.

The score area W3 displays a plurality of buttons (to be referred to as diagnostic score buttons hereinafter) B1 corresponding to a plurality of diagnostic scores.

As shown in FIGS. 4 and 5, the schema area W4 is a schema display area. The schema area W4 is divided into, for example, a long-axis schema area W41 and a short-axis schema area W42. The long-axis schema area W41 is the display area of a long-axis schema SL. In the initial screen, the long-axis schema area displays the template of a long-axis schema (to be referred to as a long-axis schema template hereinafter). The long-axis schema template is a diagram that schematically expresses the typical internal structure of the long-axis section of a carotid artery blood vessel. The long-axis schema template is set to the initial long-axis schema SL. The short-axis schema area W42 is the display area of a plurality of short-axis schemata SS corresponding to a plurality of segments, respectively. The short-axis schema area W42 includes a plurality of segment areas W421 and a plurality of additional diagnostic information areas W423. Each segment area W421 displays the short-axis schema SS of the segment. In the initial screen, each segment area W421 displays a short-axis schema template of the segment. The short-axis schema template is set to the initial short-axis schema SS. In each segment area W421, a mark (to be referred to as a long-axis section mark hereinafter) ML indicating the orientation of the long-axis section of the long-axis schema SL is displayed while overlapping the short-axis schema SS. Each additional diagnostic information area W423 displays, for the segment, a mark selected by the user via the operation unit 11 from the plurality of Doppler waveform marks MA displayed in the additional diagnostic information mark area W22. The segment name (anatomical classification name) of the segment is displayed in the vicinity, for example, on the upper side of each segment area W421 and the additional diagnostic information area W423.

Schema generation processing using the schema generation screen will be described below. The schema generation processing is divided into a reference schema generation phase and an automatic schema generation phase. The reference schema generation phase will be described first.

In the reference schema generation phase according to Example 1, a reference schema generation unit 251 generates a short-axis schema for each segment in accordance with an instruction input by the user via the operation unit 11. First, the user designates a generation target schema via the operation unit 11. For example, the user selects the name of the generation target schema from the plurality of segment names displayed in the short-axis schema area W42. Alternatively, the user selects the generation target segment area W421 from the plurality of segment areas W421 displayed in the short-axis schema area W42. A display unit 13 displays, in the drawing area W21, the short-axis schema template SS of the segment corresponding to the selected segment name or segment area W421.

An adventitial region editing button B21, an intimal region editing button B22, and a lumen region editing button B23 are displayed on the right side of the drawing area W21. When the adventitial region editing button B21 is pressed, the reference schema generation unit 251 releases deformation processing of an adventitial region R1 and prohibits a deformation operation of an intimal region R2 and deformation processing of a lumen region R3. When the intimal region editing button B22 is pressed, the reference schema generation unit 251 releases deformation processing of the intimal region R2 and prohibits deformation processing of the adventitial region R1 and deformation processing of the lumen region R3. When the lumen region editing button B23 is pressed, the reference schema generation unit 251 releases deformation processing of the lumen region R3 and prohibits deformation processing of the adventitial region R1 and deformation processing of the intimal region R2. The user performs the deformation operation for each of the adventitial region R1, the intimal region R2, and the lumen region R3. The reference schema generation unit 251 individually performs deformation processing of the adventitial region R1, the intimal region R2, and the lumen region R3 of the short-axis schema SS in accordance with the deformation operation via the operation unit 11.

The reference schema generation unit 251 has a function of coloring a schema in accordance with a diagnostic score to increase the usefulness of the schema. As described above, the score area W3 displays the plurality of diagnostic score buttons B1 corresponding to a plurality of diagnostic scores, respectively. The diagnostic scores are determined by the properties of plaques or stenosis ratio. More specifically, there exist a normal button B11 corresponding to score "normal", a homogeneous low brightness button B12 corresponding to score "homogeneous low brightness", a homogeneous high brightness button B13 corresponding to score "homogeneous high brightness", a shadow+homogeneous high brightness button B14 corresponding to score "shadow+homogeneous high brightness", a heterogeneous button B15 corresponding to score "heterogeneous", a cystic+heterogeneous button B16 corresponding to score "cystic+heterogeneous", and a depression button B17 corresponding to score "depression". To cope with a case in which the diagnostic score is undecided, an undecided score button B18 may be displayed. A color corresponding to the diagnostic score is associated with each diagnostic score button B1. The user decides the diagnostic score of the diagnosis target blood vessel by observing medical images and the like, and presses the button B1 corresponding to the decided diagnostic score via the operation unit 11. The reference schema generation unit 251 assigns the color associated with the pressed button B1 to the short-axis schema SS displayed in the drawing area W21. The reference schema generation unit 251 can thus generate a short-axis schema having the color corresponding to the diagnostic score. The colors may be assigned to all anatomical regions or only specific anatomical regions of the short-axis schema SS. For example, a color is assigned to the intimal region R2. The display unit 13 displays the short-axis schema SS in the color associated with the pressed button B1.

As shown in FIGS. 4 and 5, the score area W3 displays an "all normal button" B3. When the "all normal button" B3 is pressed via the operation unit 11, the reference schema generation unit 251 assigns the color corresponding to score "normal" to all short-axis schemata SS.

Note that not a color but a pattern may be associated with each diagnostic score button B1. In this case, the reference schema generation unit 251 can generate a short-axis schema having a pattern according to the diagnostic score.

As described above, the short-axis schema area W42 is provided with the additional diagnostic information areas W423. The additional diagnostic information areas W423 display, for example, the plurality of Doppler waveform marks MA that schematically express the typical Doppler waveforms according to the diagnostic scores or anatomical parts. The user observes the ultrasonic image or Doppler waveform of each segment and selects a Doppler waveform mark MA appropriate for each segment from the plurality of Doppler waveform marks MA via the operation unit 11. The selected Doppler waveform mark MA is displayed in the additional diagnostic information area W423 of the corresponding segment. The short-axis schema SS and the Doppler waveform mark MA concerning the same segment are stored in a schema storage unit 23 in association with each other. Since the Doppler waveform mark MA is displayed adjacent to the short-axis schema of each segment, the basis of the diagnostic score assigned to each segment can be indicated by the Doppler waveform mark MA.

As shown in FIGS. 4 and 5, a save button B41, a clear button B42, and a cancel button B43 are displayed on the upper side of the drawing area W21. When the save button B41 is pressed via the operation unit 11, the reference schema generation unit 251 sets the short-axis schema SS rendered in the drawing area W21 as the short-axis schema of the corresponding segment. The set short-axis schema is stored in the schema storage unit 23 in association with the segment name. In addition, the set short-axis schema is displayed in the segment area W421 of the corresponding segment. When the clear button B42 is pressed via the operation unit 11, the reference schema generation unit 251 replaces the short-axis schema SS rendered in the drawing area W21 with the short-axis schema template. When the cancel button B43 is pressed via the operation unit 11, the operation is undone to restore the immediately preceding state.

The plurality of short-axis schemata of the plurality of segments are generated using such various functions on the schema generation screen.

Processing of the automatic schema generation phase will be described next.

Figure 6:
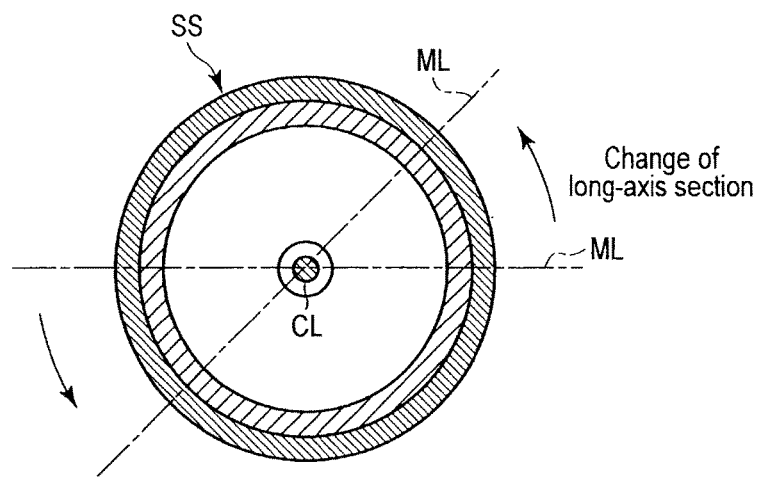
FIG. 6 is a view for explaining an operation of changing the orientation of the long-axis section according to Example 1.

Triggered by generation of the plurality of short-axis schemata of the plurality of segments, an automatic schema generation unit 253 automatically generates a long-axis schema by image processing based on the plurality of short-axis schemata. The long-axis section of the long-axis schema can arbitrarily be set in accordance with a user instruction input via the operation unit 11. As described above, the long-axis section mark ML indicating the orientation of the long-axis section is displayed for the short-axis schema SS of each segment area W421. As shown in FIG. 6, the orientation of the long-axis section mark ML can be changed by the user via the operation unit 11. More specifically, the long-axis section mark ML is rotated about the central axis CL via the operation unit 11. The automatic schema generation unit 253 changes the long-axis section of the long-axis schema in synchronism with the changing operation of the long-axis section mark ML. The orientation of the long-axis section can be the same for all segments or change between the segments. If the orientation of the long-axis section is the same for all segments, the changing operation of one long-axis section mark ML is automatically reflected on the long-axis sections of all segments.

Figure 7:
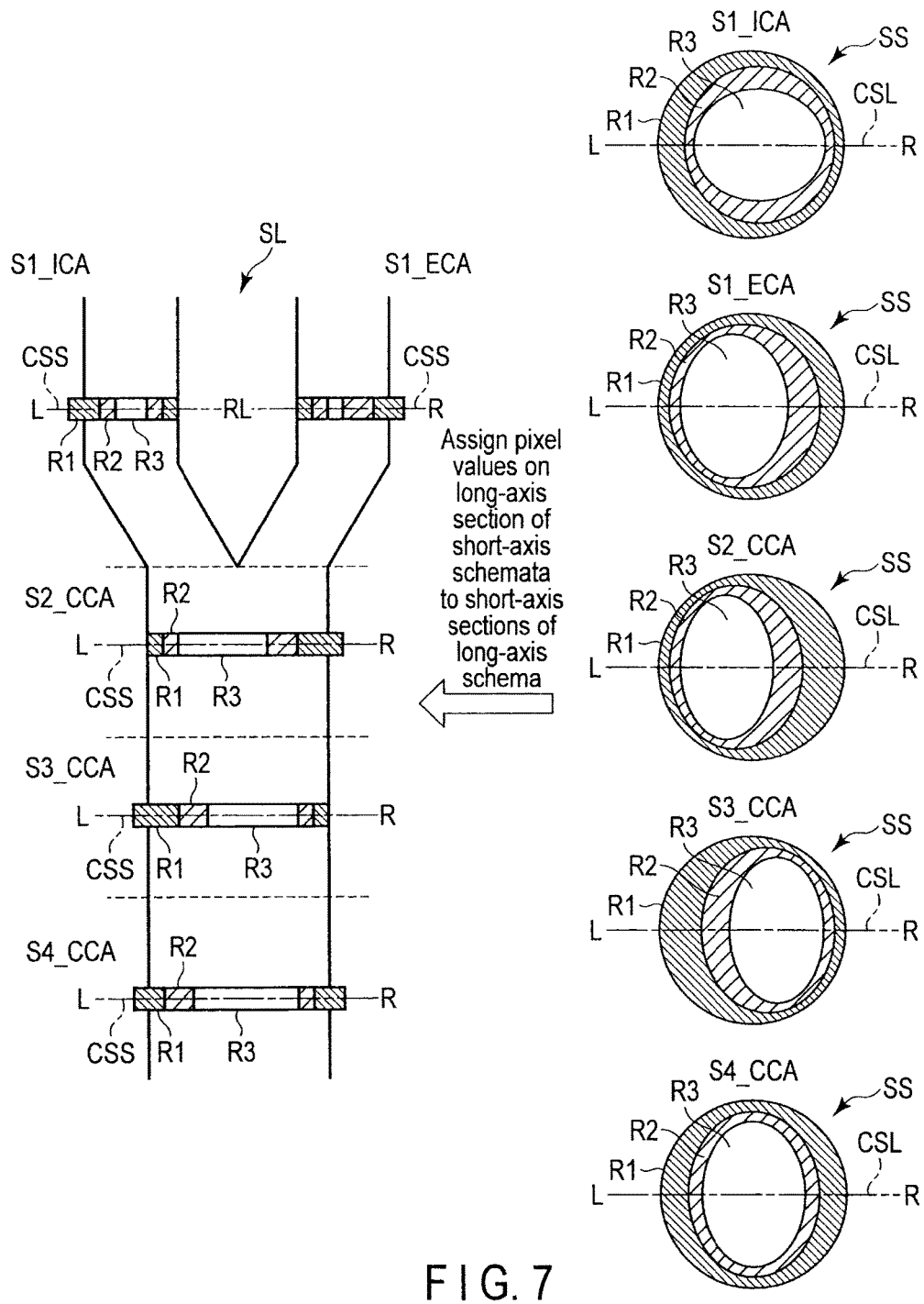
FIG. 7 is a view showing assignment processing included in automatic schema generation processing performed by the automatic schema generation unit shown in FIG. 2.

The automatic schema generation processing by the automatic schema generation unit 253 includes assignment processing and smoothing processing. FIG. 7 is a view showing assignment processing by the automatic schema generation unit 253. As shown in FIG. 7, a short-axis section CSS of each segment is typically set to be perpendicular to the center of the central axis in each segment of the long-axis schema SL. Referring to FIG. 7, a long-axis section CSL of each segment is oriented in the same direction and, more specifically, in the horizontal direction. The pixels of the long-axis section CSL on the short-axis schema SS are associated with the pixels of the short-axis section CSS on the long-axis schema SL, which anatomically match the pixels of the long-axis section CSL. In assignment processing, the automatic schema generation unit 253 assigns the pixel values of the anatomical regions R1, R2, and R3 on the long-axis section CSL of each short-axis schema SS to the anatomical same positions on the long-axis schema SL. More specifically, for each short-axis schema SS, the automatic schema generation unit 253 assigns the pixel values of the pixels on the long-axis section CSL of the short-axis schema SS to the pixels that exist on the short-axis section CSS for the short-axis schema SS in the long-axis schema SL at the same anatomical positions as the pixels of the long-axis section CSL. Smoothing processing is then performed.

Figure 8:
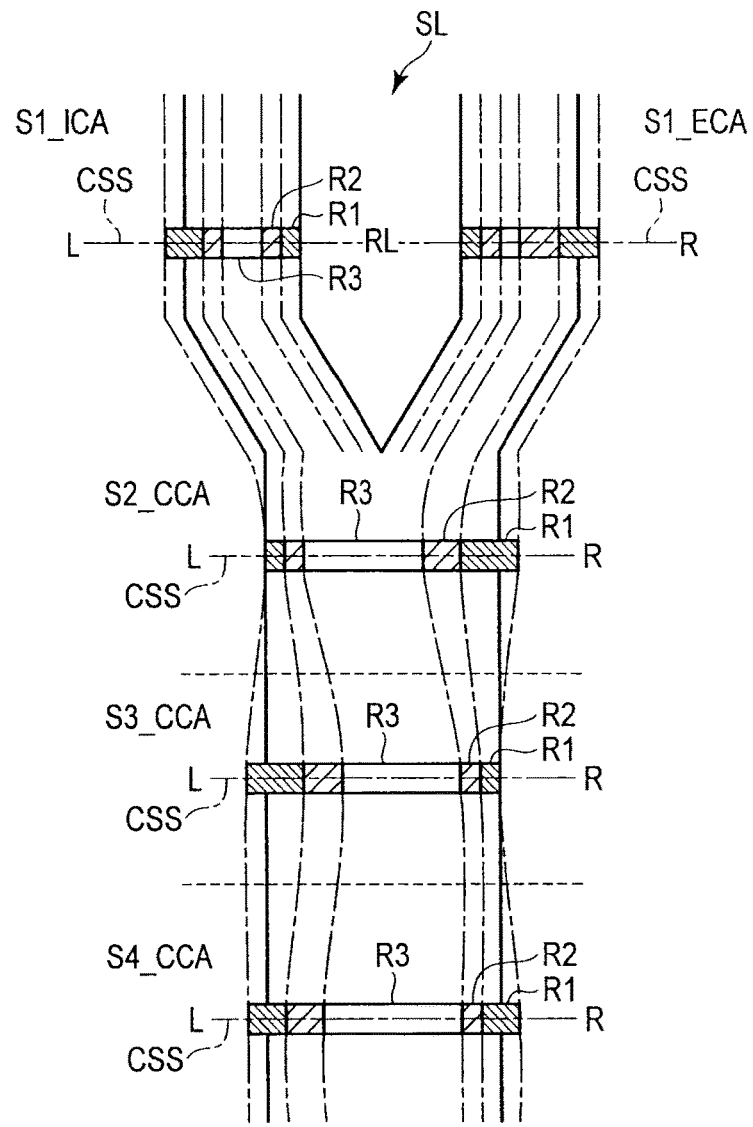
FIG. 8 is a view showing smoothing processing included in automatic schema generation processing performed by the automatic schema generation unit shown in FIG. 2.

In the smoothing processing, the automatic schema generation unit 253 performs geometric smoothing processing within the long-axis section for each of the plurality of anatomical regions R1, R2, and R3, as shown in FIG. 8. The smoothing processing is performed using an arbitrary smoothing function such as a sigmoid function or a spline function. With the smoothing processing, the anatomical regions R1, R2, and R3 assigned to only the short-axis sections CSS are assigned to the whole range of the long-axis schema SL so as to smoothly connect the anatomical regions R1, R2, and R3 on the short-axis schemata SS. If different diagnostic scores are assigned in the plurality of short-axis schemata SS, different color values are assigned to the anatomical regions R1, R2, and R3 of the same types on different short-axis schemata. In this case, smoothing processing of color values is performed. With this processing, a color gradation is formed between two short-axis sections CSS on the long-axis schema SL. The long-axis schema SL is thus generated based on the plurality of short-axis schemata of the plurality of sections.

Note that to more naturally render the anatomical regions at the boundary between the inner (right in FIGS. 7 and 8) blood vessel wall of the blood vessel of a section S1_ICA and the inner (left in FIGS. 7 and 8) blood vessel wall of the blood vessel of a section S1_ECA, that is, the blood vessel branch portion, the automatic schema generation unit 253 performs interpolation processing to be described below.

Figure 9:
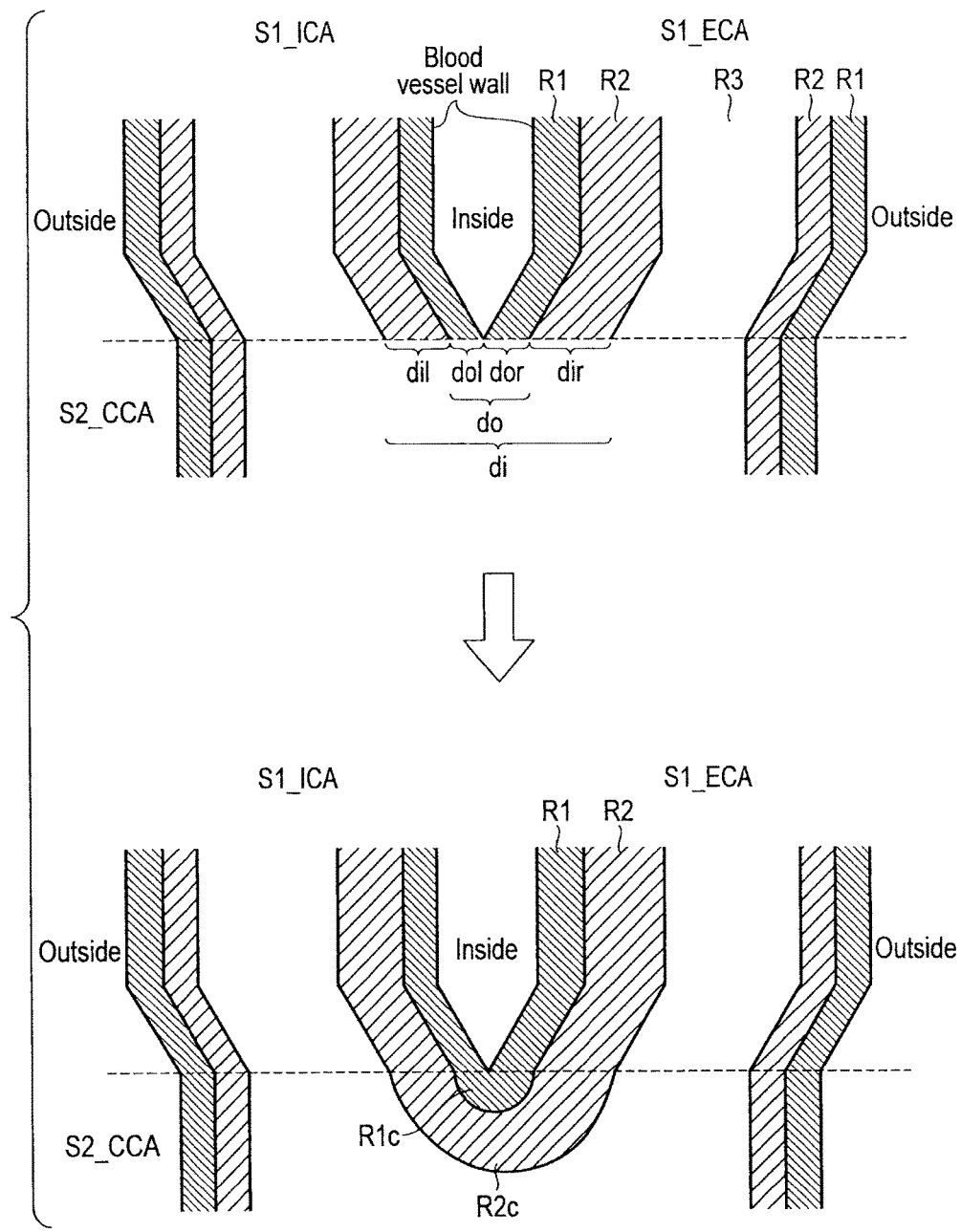
FIG. 9 is a view showing interpolation processing at a blood vessel branch portion included in automatic schema generation processing performed by the automatic schema generation unit shown in FIG. 2.

FIG. 9 is a view for explaining interpolation processing at the blood vessel branch portion. As shown in FIG. 9, the anatomical regions R1 and R2 concerning the inner (right in FIG. 9) blood vessel wall of the blood vessel of the section S1_ICA and anatomical regions R1 and R2 concerning the inner (left in FIG. 9) blood vessel wall of the blood vessel of the section S1_ECA are discontinuous before execution of the interpolation processing. The automatic schema generation unit 253 interpolates the pixel value missing parts in a section S2_CCA between the anatomical regions R1 and R2 concerning the inner blood vessel wall of the section S1_ICA and anatomical regions R1 and R2 concerning the inner blood vessel wall of the section S1_ECA by a circle having the sum of the thicknesses of the anatomical regions R1 and R2 concerning the inner blood vessel walls of the sections as the diameter. Let dol be the width of the inner adventitial region R1 of the section S1_ICA, dil be the width of the intimal region R2, dor be the width of the inner adventitial region R1 of the section S1_ECA, and dir be the width of the intimal region R2. The automatic schema generation unit 253 interpolates the missing part of the adventitial region R1 derived from the blood vessel of the section S2_CCA by a circle R1c having a sum do of the widths dol and dor as the diameter. The inside of the circle R1c is set as the adventitial region. In a similar manner, the automatic schema generation unit 253 interpolates the missing part of the intimal region R2 derived from the blood vessel of the section S2_CCA by a circle R2c having a sum di of the widths dil, dol, dor, and dir as the diameter. A portion that exists inside the circle R2c and does not overlap the circle R1c is set as the intimal region R2. With the interpolation processing, the missing parts of the anatomical regions R1 and R2 at the branch portion are interpolated.

In the above-described way, the automatic schema generation unit 253 can generate a single long-axis schema concerning a single long-axis section based on a plurality of short-axis schemata. The generated long-axis schema is stored in the schema storage unit 23 in association with the short-axis schemata. The generated long-axis schema is also displayed in the long-axis schema area W41 by the display unit 13. Note that an example has been described above in which a single long-axis schema concerning a single long-axis section is generated based on a plurality of short-axis schemata. However, the embodiment is not limited to this. For example, the automatic schema generation unit 253 may set a plurality of long-axis sections having different rotation angles about the central axis and individually generate the plurality of long-axis schemata concerning the plurality of long-axis sections based on the plurality of short-axis schemata by the above-described method.

As shown in FIGS. 4 and 5, the score area W3 displays an attach button B51 and a close button B52. When the attach button B51 is pressed via the operation unit 11, the medical reading report preparing unit 17 attaches the generated short-axis schemata and long-axis schemata to the medical reading report. The medical reading report to which the short-axis schemata and long-axis schemata are attached is stored in the medical reading report storage unit 21. When the close button B52 is pressed via the operation unit 11, the display unit 13 erases the schema generation screen from the display device.

As described above, the medical reading report preparing apparatus 1 according to Example 1 can automatically generate a long-axis schema or long-axis schemata based on a plurality of short-axis schemata manually generated in accordance with a deformation operation via the operation unit 11.

Example 2

A short-axis schema according to Example 2 is selected from candidates of short-axis schemata (to be referred to as short-axis schema candidates hereinafter) generated in advance in accordance with a user instruction. A medical reading report preparing apparatus 1 according to Example 2 will be described below. Note that the medical reading report preparing apparatus 1 according to Example 2 generates a long-axis schema based on short-axis schemata using the same method according to Example 1. Hence, in Example 2, only generation (selection) of the short-axis schema will be described. The same reference numerals as in Example 1 denote constituent elements having almost the same functions in the following explanation, and a description thereof will be repeated only when necessary.

Figure 10:
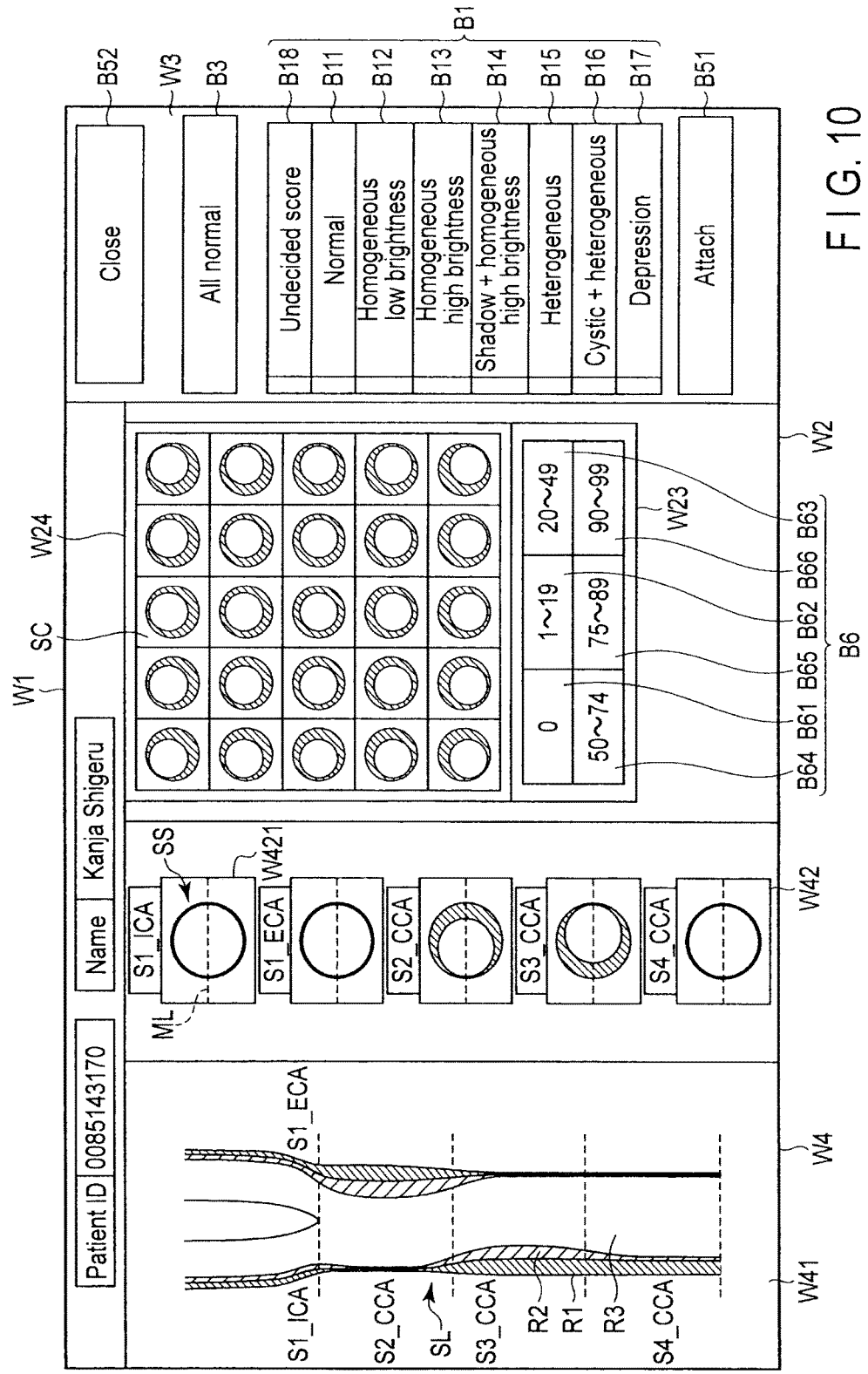
FIG. 10 is a view showing a schema generation screen displayed by a display unit according to Example 2.

FIG. 10 is a view showing a schema generation screen displayed by a display unit 13 according to Example 2. As shown in FIG. 10, a schema generation area W2 of the schema generation screen according to Example 2 includes a stenosis ratio range area W23 and a schema candidate area W24. The stenosis ratio range area W23 is a display area for a plurality of stenosis ratio range buttons B6 corresponding to a plurality of stenosis ratio ranges. The stenosis ratio is an index that represents the ratio of the intimal region with respect to the blood vessel region in a short-axis section in terms of percentage. The stenosis ratio range is one of indices used to evaluate the malignancy of a plaque. FIG. 10 illustrates, for example, a stenosis ratio button B61 concerning a stenosis ratio range "0", a stenosis ratio button B62 concerning a stenosis ratio range "1 to 19", a stenosis ratio button B63 concerning a stenosis ratio range "20 to 49", a stenosis ratio button B64 concerning a stenosis ratio range "50 to 74", a stenosis ratio button B65 concerning a stenosis ratio range "75 to 89", and a stenosis ratio button B66 concerning a stenosis ratio range "90 to 99". The schema candidate area W24 is a display area for a plurality of short-axis schema candidates SC.

Short-axis schema generation processing according to Example 2 will be described below in detail with reference to FIG. 10. A schema storage unit 23 according to Example 2 stores the plurality of short-axis schema candidates SC. Each of the plurality of short-axis schema candidates SC is stored in association with the stenosis ratio range corresponding to the short-axis schema candidate. Each short-axis schema candidate SC has a stenosis ratio according to the associated stenosis ratio range. A plurality of short-axis schema candidates SC concerning the same stenosis ratio range include intimal regions whose shapes and positions are different from each other.

In a short-axis schema generation phase, first, the user selects the section of the short-axis schema of the generation target via an operation unit 11 according to the same method as described above. The user also presses, via the operation unit 11, the stenosis ratio button B6 corresponding to the stenosis ratio range to which the diagnosis target blood vessel belongs. The display unit 13 reads out the plurality of short-axis schema candidates SC associated with the stenosis ratio range corresponding to the pressed stenosis ratio button B6 from the schema storage unit 23 and displays the short-axis schema candidates. The stenosis ratio range can be determined by the user by observing an ultrasonic image. Alternatively, a stenosis ratio calculated and displayed by an ultrasonic diagnostic apparatus 100 may be employed. Otherwise, the data of a stenosis ratio calculated by the ultrasonic diagnostic apparatus 100 based on an ultrasonic image may be received via a transmitting/receiving unit 15, and the display unit 13 may automatically display the plurality of short-axis schema candidates SC associated with the stenosis ratio range belonging to the received stenosis ratio. The user displays the plurality of displayed short-axis schema candidates SC in the schema candidate area W24. The user selects, out of the plurality of short-axis schema candidates SC displayed in the schema candidate area W24, the short-axis schema candidate SC most approximate to the internal structure of the diagnosis target blood vessel via the operation unit 11. A reference schema generation unit 251 sets the selected short-axis schema candidate SC to a short-axis schema SS of the section of the generation target. The short-axis schema of each section is thus selected out of the plurality of short-axis schema candidates SC, thereby generating a plurality of short-axis schemata SS.

Note that in Example 2 as well, a color or a pattern can be assigned to each short-axis schema SS by pressing a diagnostic score button B1, as in Example 1.

As described above, the medical reading report preparing apparatus 1 according to Example 2 can automatically generate a long-axis schema based on a plurality of short-axis schemata manually selected from a plurality of short-axis schema candidates.

Example 3

In Examples 1 and 2, the medical reading report preparing apparatus 1 automatically generates a long-axis schema based on short-axis schemata. A medical reading report preparing apparatus 1 according to Example 3 automatically generates short-axis schemata based on long-axis schemata. The medical reading report preparing apparatus 1 according to Example 3 will be described below. The same reference numerals as in Examples 1 and 2 denote constituent elements having almost the same functions in the following explanation, and a description thereof will be repeated only when necessary.

A reference schema generation unit 251 according to Example 3 generates a plurality of long-axis schemata concerning a plurality of long-axis sections in accordance with a user instruction input via an operation unit 11. As many long-axis schemata as possible are preferably generated from the viewpoint of short-axis schema accuracy improvement by an automatic schema generation unit 253. In addition, to improve the accuracy of short-axis schemata, the plurality of long-axis sections are preferably set evenly about the rotation axis. If there are two short-axis schemata, the two short-axis sections are preferably set to be perpendicular to each other. In Example 3, the long-axis schemata can be either generated in accordance with the deformation operation of the anatomical regions via the operation unit 11, as in Example 1, or selected from a plurality of long-axis schema candidates. The long-axis schema generation method is the same as the short-axis schema generation method according to Examples 1 and 2, and a description thereof will be omitted.

Triggered by generation of the plurality of long-axis schemata, the automatic schema generation unit 253 automatically generates a plurality of short-axis schemata concerning a plurality of short-axis sections by image processing based on the plurality of generated long-axis schemata. As in Examples 1 and 2, the automatic schema generation processing of Example 3 includes assignment processing and smoothing processing. Note that for a specific description, the automatic schema generation unit 253 is assumed to generate five short-axis schemata of five segments based on two long-axis schemata concerning long-axis sections perpendicular to each other. The five segments are the same as in Examples 1 and 2.

Figure 11:
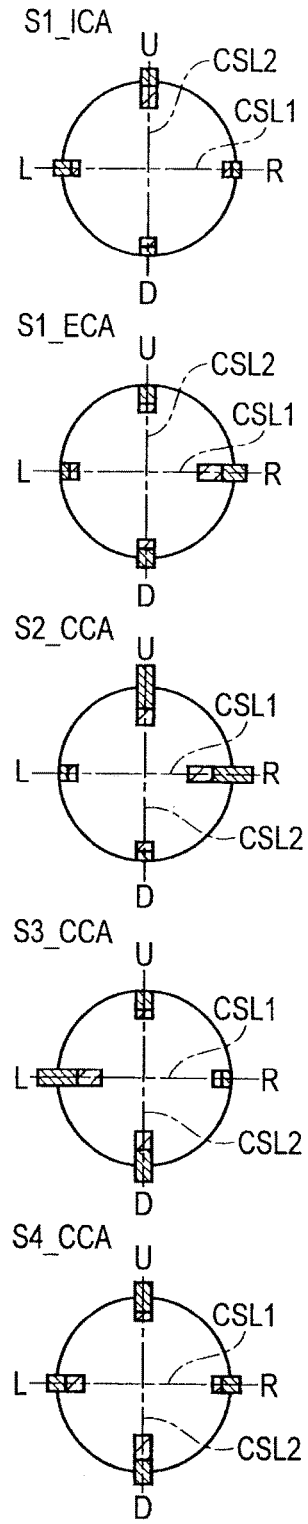
FIG. 11 is a view showing assignment processing included in automatic schema generation processing performed by an automatic schema generation unit according to Example 3.

FIG. 11 is a view for explaining assignment processing according to Example 3. As shown in FIG. 11, a long-axis schema SL1 concerning a long-axis section SCL1 and a long-axis schema SL2 concerning a long-axis section SCL2 are generated. In assignment processing, the automatic schema generation unit 253 assigns the pixel values of anatomical regions R1, R2, and R3 on a short-axis section CSS of each section of the long-axis schemata SL1 and SL2 to the same anatomical positions on each short-axis schema SS. That is, the automatic schema generation unit 253 assigns the pixel values of the pixels on the short-axis section CSS of the long-axis schema SL1 to the pixels located at the same anatomical positions on a long-axis section CSL1 in each short-axis schema SS. In addition, the automatic schema generation unit 253 assigns the pixel values of the pixels on the short-axis section CSS of the long-axis schema SL2 to the pixels located at the same anatomical positions on a long-axis section CSL2 in each short-axis schema SS. Smoothing processing is then performed.

Figure 12:
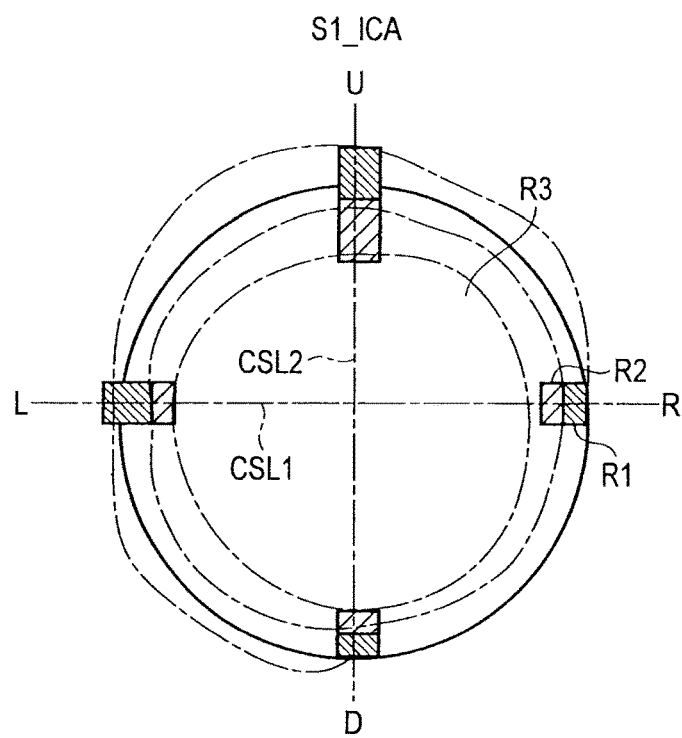
FIG. 12 is a view showing smoothing processing included in automatic schema generation processing performed by the automatic schema generation unit according to Example 3.

FIG. 12 is a view for explaining smoothing processing performed by the automatic schema generation unit 253. Note that for the sake is simplicity, FIG. 12 illustrates only the short-axis schema concerning a section S1_ICA. In smoothing processing, the automatic schema generation unit 253 performs geometric smoothing processing for each of a plurality of anatomical regions R1, R2, and R3 along the short-axis section, as shown in FIG. 12. The smoothing processing is the same as in Examples 1 and 2. With the smoothing processing, the anatomical regions R1, R2, and R3 assigned to only the long-axis sections CSL1 and CSL2 are assigned to the whole range of the short-axis schema SS so as to smoothly connect the anatomical regions R1, R2, and R3 on the short-axis section CSS. The short-axis schema concerning another section is generated by the same method described above.

In the above description, the automatic schema generation unit 253 generates a plurality of short-axis schemata based on two long-axis schemata concerning two long-axis sections perpendicular to each other. However, the automatic schema generation unit 253 according to Example 3 is not limited to this. The automatic schema generation unit 253 according to Example 3 may automatically generate a plurality of short-axis schemata concerning a plurality of short-axis sections based on three or more long-axis schemata concerning three or more long-axis sections using the same method as described above. The larger the number of long-axis schemata is, the higher the accuracy of short-axis sections is.

As described above, the medical reading report preparing apparatus 1 according to Example 3 can automatically generate a short-axis schema based on a plurality of long-axis schemata.

[Effects]

As described above, the medical reading report preparing apparatus 1 according to this embodiment includes the schema storage unit 23 and the schema processing unit 25. The schema storage unit 23 stores a reference schema that schematically expresses the internal structure of a diagnosis target blood vessel concerning the reference section of the diagnosis target blood vessel. The schema processing unit 25 automatically generates a schema concerning a section that crosses the reference section of the diagnosis target blood vessel based on the reference schema.

With this arrangement, the medical reading report preparing apparatus 1 according to the embodiment can automatically generate another schema based on one schema without individually manually generating both the short-axis schema and the long-axis schema.

According to this embodiment, it is therefore possible to reduce the working load of the user in schema generation.

Additionally, according to this embodiment, mismatching between the short-axis schema and the long-axis schema is reduced as compared to a case in which the short-axis schema and the long-axis schema are individually manually generated.

(Modification)

In this embodiment, the medical reading report preparing apparatus 1 is a computer apparatus connected to the medical image diagnostic apparatus 100 via a network. However, the medical reading report preparing apparatus 1 according to this embodiment is not limited to this. For example, the medical reading report preparing apparatus 1 may be incorporated in the medical image diagnostic apparatus 100. When the medical reading report preparing apparatus 1 is incorporated in the medical image diagnostic apparatus 100, the medical image diagnostic apparatus 100 can be an image diagnostic apparatus of any type such as an ultrasonic diagnostic apparatus, an X-ray diagnostic apparatus, an X-ray computed tomography apparatus, a magnetic resonance diagnostic apparatus, or a nuclear medicine diagnostic apparatus. However, the medical image diagnostic apparatus 100 is assumed to be an ultrasonic diagnostic apparatus for a specific description. The medical image diagnostic apparatus 100 incorporating the medical reading report preparing apparatus 1 will be described below as a modification. Note that the same reference numerals as in this embodiment denote constituent elements having almost the same functions in the following explanation, and a description thereof will be repeated only when necessary.

Figure 13:
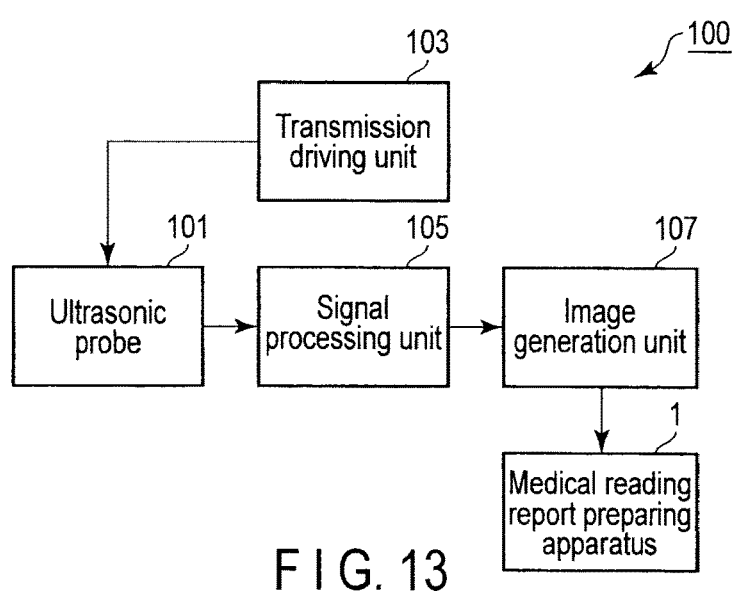
FIG. 13 is a block diagram showing the arrangement of an ultrasonic diagnostic apparatus according to a modification.

FIG. 13 is a block diagram showing the arrangement of the ultrasonic diagnostic apparatus 100 according to the modification. As shown in FIG. 13, the ultrasonic diagnostic apparatus 100 includes an ultrasonic probe 101, a transmission driving unit 103, a signal processing unit 105, and an image generation unit 107.

A transducer array is incorporated on the distal end side of the ultrasonic probe 101. The transducer array includes a plurality of transducers arranged one- or two-dimensionally. The transducer transmits/receives an ultrasonic wave. More specifically, the transducer receives a driving signal from the transmission driving unit 103. Upon receiving the transducer driving signal, the transducer transmits an ultrasonic wave, receives the ultrasonic wave reflected by the object, and generates an echo signal corresponding to the received ultrasonic wave. The generated echo signal is supplied to the signal processing unit 105.

The transmission driving unit 103 scans the diagnosis target blood vessel by the ultrasonic wave via the ultrasonic probe 101. More specifically, the transmission driving unit 103 applies a driving signal given a delay time according to the transmission direction and the transmission focal point to the transducer. When the driving signal is applied, the ultrasonic probe 101 transmits an ultrasonic transmission wave concerning the transmission direction and the transmission focal point according to the delay time.

The signal processing unit 105 performs A/D conversion of the echo signal from the ultrasonic probe 101. The signal processing unit 105 gives the digital echo signal a delay time necessary for deciding the beam direction of an ultrasonic reception beam for each reception focal point and adds the echo signals each given the delay time. With this delay addition, a reception signal corresponding to the ultrasonic reception beam is generated.

The image generation unit 107 immediately repetitively generates an ultrasonic image concerning the scan region based on the reception signal. The ultrasonic image according to this embodiment can be of any type such as a B-mode image, a Doppler waveform, or a color Doppler image that can be generated by the ultrasonic diagnostic apparatus 100. The generated ultrasonic image is immediately supplied to the medical reading report preparing apparatus 1 incorporated in the ultrasonic diagnostic apparatus 100.

The medical reading report preparing apparatus 1 according to this modification displays the ultrasonic images repetitively supplied from the image generation unit 107 as a moving image, and also displays a report creation screen or a schema generation screen as described in the embodiment. This allows the user to perform a medical image creation operation or a schema generation operation while observing the ultrasonic images.

Hence, the medical image diagnostic apparatus according to this modification can reduce the working load of the user in schema generation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical reading report preparing apparatus comprising:
processing circuitry configured to
generate a predetermined number of first schemas, the first schemas being diagrams that schematically express an internal structure of a diagnosis target blood vessel concerning a first section of the diagnosis target blood vessel, and
automatically generate a second schema by image processing with response to the generation of the predetermined number of the first schemas, the second schema being a diagram that expresses an internal structure of the diagnosis target blood vessel concerning a second section crossing the first section; and
a display configured to display the first schemas and the second schema for assisting a medical report creation, wherein
the first schemas and the second schema comprise a short-axis schema concerning a short-axis section of the target blood vessel, and the display is configured to display a Doppler waveform mark selected by a user instruction adjacently to the short-axis schema.

2. The medical reading report preparing apparatus according to claim 1, wherein each of the predetermined number of the first schemas and the second schema include a plurality of anatomical regions classified in accordance with anatomical properties of a blood vessel.

3. The medical reading report preparing apparatus according to claim 2, wherein the plurality of anatomical regions include an adventitial region, an intimal region, and a lumen region.

4. The medical reading report preparing apparatus according to claim 2, wherein
each of the predetermined number of the first schemas includes a plurality of short-axis schemata concerning a plurality of short-axis sections of the diagnosis target blood vessel,
the second schema includes a long-axis schema concerning a long-axis section of the diagnosis target blood vessel, and
the processing circuitry generates the long-axis schema based on the plurality of short-axis schemata.

5. The medical reading report preparing apparatus according to claim 4, wherein the processing circuitry generates the long-axis schema by smoothing processing aiming at each of the plurality of anatomical regions for the plurality of short-axis schemata along the long-axis section.

6. The medical reading report preparing apparatus according to claim 4, further comprising:
input circuitry configured to input an instruction to deform the plurality of anatomical regions in the template, wherein
the display displays a template of a schema that schematically expresses a typical internal structure of a blood vessel concerning a short-axis section, and
the processing circuitry individually generates the plurality of short-axis schemata by deforming the anatomical regions in the template in accordance with the instruction for each of the plurality of short-axis sections.

7. The medical reading report preparing apparatus according to claim 4, further comprising:
a first memory configured to store a plurality of schema candidates concerning a short-axis section, each of the plurality of schema candidates having a plurality of anatomical regions of different shapes, wherein
the processing circuitry individually generates the plurality of short-axis schemata, in accordance with a schema candidate selected by a user instruction, out of the plurality of schema candidates for each of the plurality of short-axis sections.

8. The medical reading report preparing apparatus according to claim 7, wherein, for each of the plurality of schema candidates, a shape of the internal structure depends on a stenosis ratio.

9. The medical reading report preparing apparatus according to claim 8, wherein
the memory stores the plurality of schema candidates in association with a plurality of stenosis ratio ranges respectively,
the display displays only schema candidates of the plurality of schema candidates that are associated with one of a stenosis ratio range selected by another user instruction and a stenosis ratio range that includes a stenosis ratio calculated based on a medical image of the diagnosis target blood vessel, the displayed schema candidates being extracted out of the plurality of schema candidates for each of the plurality of short-axis sections, and the processing circuitry individually generates the plurality of short-axis schemata in accordance with the schema candidate selected by the user instruction, the schema candidate being selected out of the displayed schema candidates.

10. The medical reading report preparing apparatus according to claim 9, wherein the display displays a plurality of buttons corresponding to the plurality of stenosis ratio ranges, respectively.

11. The medical reading report preparing apparatus according to claim 4, wherein the processing circuitry generates the long-axis schema concerning a long-axis section in an orientation according to the user instruction based on the plurality of short-axis schemata.

12. The medical reading report preparing apparatus according to claim 2, wherein each of the predetermined number of the first schemas includes a plurality of long-axis schemata concerning a plurality of long-axis sections of the diagnosis target blood vessel, and the processing circuitry generates the short-axis schema based on the plurality of long-axis schemata.

13. The medical reading report preparing apparatus according to claim 12, wherein the processing circuitry generates the short-axis schema by smoothing processing aiming at each of the plurality of anatomical regions for the plurality of long-axis schemata in the short-axis section.

14. The medical reading report preparing apparatus according to claim 1, further comprising a second memory configured to store a medical reading report to which each of the predetermined number of the first schemas and the second schema are attached.

15. The medical reading report preparing apparatus according to claim 1, wherein each of the predetermined number of the first schemas and the second schema have one of a color and a pattern corresponding to a diagnostic score selected in accordance with a user instruction.

16. The medical reading report preparing apparatus according to claim 15, wherein the display displays a plurality of buttons corresponding to the plurality of diagnostic scores, respectively, and each of the predetermined number of the first schemas and the second schema have one of a color and a pattern corresponding to the button selected in accordance with a user instruction out of the plurality of buttons.

17. A medical image diagnostic apparatus comprising:

processing circuitry configured to, generate a medical image of a diagnosis target blood vessel, generate a predetermined number of first schemas, the first schemas being diagrams that schematically express an internal structure of a diagnosis target blood vessel concerning a first section of the diagnosis target blood vessel, and automatically generate a second schema by image processing with response to the generation of the predetermined number of the first schemas, the second schema being a diagram that expresses an internal structure of the diagnosis target blood vessel concerning a second section crossing the first section; and a display configured to display the first schemas and the second schema for assisting a medical report creation, wherein the first schemas and the second schema comprise a short-axis schema concerning a short-axis section of the target blood vessel, and the display is configured to display a Doppler waveform mark selected by a user instruction adjacently to the short-axis schema.

* * * * *